United States Patent [19]

Nashed et al.

[11] 4,329,366

[45] May 11, 1982

[54] TOPICAL ACYLAMINOPHENOLS

[75] Inventors: Wilson Nashed, North Brunswick; David T. Rovee, Bridgewater; Robert J. Gander, Whitehouse, all of N.J.

[73] Assignee: Johnson & Johnson Products, Inc., New Brunswick, N.J.

[21] Appl. No.: 239,862

[22] Filed: Mar. 2, 1981

Related U.S. Application Data

[62] Division of Ser. No. 92,296, Nov. 8, 1979, abandoned.

[51] Int. Cl.$^3$ ............................................ A61K 31/165
[52] U.S. Cl. .................................................... 424/324
[58] Field of Search ..................... 424/324; 260/404.5, 260/405; 564/223

[56] References Cited

U.S. PATENT DOCUMENTS

| | | | |
|---|---|---|---|
| 2,799,692 | 7/1957 | Croxall et al. | 564/223 |
| 3,081,321 | 3/1963 | Young | 260/404 |
| 4,102,995 | 7/1978 | Hebborn | 424/230 |

FOREIGN PATENT DOCUMENTS 7.624M 1/1970 France .

OTHER PUBLICATIONS

Chem. Abst. 88-58567y, (1978).
Merds Index-9th Ed., (1976), p. 433.

*Primary Examiner*—Stanley J. Friedman
*Attorney, Agent, or Firm*—Irving Newman

[57] ABSTRACT

Treatment of inflammation by applying topically a selected acylaminophenol in a pharmaceutically acceptable topical vehicle.

11 Claims, No Drawings

TOPICAL ACYLAMINOPHENOLS

CROSS-REFERENCE TO RELATED APPLICATIONS

This application is a division of our copending application Ser. No. 92,296, filed Nov. 8, 1979, now abandoned.

TECHNICAL FIELD

This invention relates to topical pharmaceutical compositions for the treatment of cutaneous or mucous membrane disorders characterized by irritation or inflammation. More specifically, the invention comprises treatment of such disorders by topical application to the affected area of a selected acylaminophenol in a suitable vehicle.

BACKGROUND ART

There are many steroidal drugs suitable for treating particular responsive dermatological disorders. They have a broad range of applicable biological activities (e.g. cell membrane stabilization, vasoconstrictor activity, anti-mitotic effect, suppression of DNA and protein synthesis, etc.). However, steroids often exhibit undesired local and systemic side effects when used for prolonged periods. These may be manifested in the form of local skin atrophy, or in adrenal atrophy in the most severe case. Furthermore, a reduction in host defense mechanisms to infection may accompany their use.

Beyond the potential undesired side effects, steroids do not interact with the complete biological spectrum of inflammation. For example, ultraviolet (UV) light induced erythema is not amenable to treatment by steroidal anti-inflammatories. UV-induced early changes in skin such as vasodilation are related to the conversion of arachidonic acid to E prostaglandins or to intermediate forms such as HETE (12L-hydroxy-5,8,10,14-eicosatetraenoic acid) or the endoperoxides which are vasoactive and are believed to have cutaneous activity, such as triggering hyperproliferative epidermal activity. See, for example, Bem, J. L. and Greaves, M. W. 1974 Prostaglandin $E_1$ effects on epidermal cell growth "in vitro." *Arch. Derm. Forsch.* 251:35–41; Snyder, D. S. and Eaglstein, W. H. 1974 Topical indomethacin and sunburn. *Brit. J. Derm.* 90:91–93; Snyder, D. S. and Eaglstein, W. H. 1974 Intradermal anti-prostaglandin agents and sunburn. *J. Invest. Derm.* 62.47–50; and Goldyne, M. E. et al. 1973 Prostaglandin activity in human cutaneous inflammation: Detection by radio-immunoassay. *Prostaglandins* 4:737–749. See also Hsia, S. L., Ziboh, V. A. and Snyder, D. S. 1974. Naturally occurring and synthetic inhibitors of prostaglandin synthetase of the skin. *Prostaglandin Synthetase Inhibitors* 353–361. Although it is not understood completely, it is thought that these effects related to prostaglandin biosynthesis are important components of many dermatopathologies, so a drug which will interfere with this biosynthesis should be useful in the clinical improvement of the disease.

There are many non-steroidal compounds or agents which also have anti-inflammatory effects. Many of these are believed to act by blocking the prostaglandin synthetase complex of enzymes that are present in normal skin and are necessary for the biosynthetic processes described above. Furthermore, as a general rule, these drugs are relatively free of unwanted side effects. Examples of such non-steroidal anti-inflammatory compounds include aspirin, indomethacin, suprofen, cliprofen and ethyl 5-p-chlorobenzoyl-1, 4-dimethylpyrrole-2-acetate. While many acylaminophenols, including the compounds employed in the treatment of the present invention, have been reported in the literature and used for a variety of purposes, to our knowledge, none have heretofore been reported to be useful as topical anti-inflammatory agents. A review of Chemical Abstracts has revealed the following disclosures relevant to pharmaceutical activities of related aminophenols as well as pharmaceutical and nonpharmaceutical activities of the substituted aminophenols specified below as being useful in the topical compositions and methods of the present invention. CA 57 16492 (1962) contains a report of anti-rheumatic activity for N-nicotinyl-p-aminophenol and N-succinyl-p-aminophenol, and refers to Austrian Pat. No. 222,647 (1962). p-Aminophenol amides of sperm head oil acids and sperm blubber oil acids, mentioned in Netherlands patent application No. 6,505,431 as having hypocholesterolemic activity, are reported at CA 64 14137 (1966). U.S. Pat. No. 3,081,321 is reported at CA 60 2833 (1964) to disclose analgesic activity of p-aminophenol amides of aliphatic monocarboxylic acids. Analgesic, anti-pyretic and anti-inflammatory activities are attributed to the dipropyl acetyl amide of p-aminophenol at CA 76 153384x (1972), which refers to French M 7624 to Laboratories J. Berthier (1970); and the same activities are reported for the cystein derivative of p-aminophenol at CA 86 107003f (1977), an abstract of an article by Portelli, Renzi, Cervato & Frigeni, Farmaco, Ed. Sci. 31 (11) 767–775 (1976). According to CA 86 43215s (1977), Belgian Pat. No. 834,304 reports that aryl amides of omega-aminoalkanoic acids, having the formula

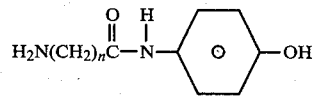

wherein n is 4, 5, 6 or 8, inhibit blood platelet aggregation. CA 89 108193s (1978) has the same report with reference to British Pat. No. 1,498,996, apparently a counterpart of the above Belgian patent. CA 88 58568z (1978) reports that a Japanese patent publication (Kokai No. 77,110,835) discloses that certain benzanilide derivatives (none of which are 4-acylaminophenols, however) have shown anti-inflammatory activity when administered to mice orally or injected i.p.

Salicylaminophenol, which has the structure:

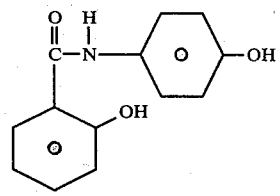

[also named 4'-hydroxysalicylanilide; N-(p-hydroxyphenyl) salicylamide, and N-salicoylaminophenol], has been reported to have choleretic activity (Merck Index, Ninth Edition, 6724, page 894); fungistatic activity in vitro [CA 71 69577b, (1969)]; activity in inhibiting allergic reaction or inflammation in mice when administered orally or i.p. [CA 88 58568z, (1978)]; molluscocidal and cercaricidal activity [CA 89 192405t, (1978)]; a photosensitizing effect in guinea pigs [CA 83 37501d, (1975)]; anthelminthic activity [CA 80 133081a, (1974)]and utility as an antioxidant for unsaturated rubber [CA 91 6227e, (1979)].

For the acylaminophenols used in the composition and treatment of the present invention, having the formula:

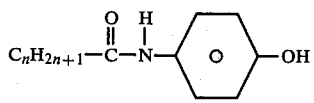

wherein n is an integer from 5 to 11, inclusive and closely related structural analogs (wherein n is less than 5 or greater than 11) the following activities have been reported:

n=2 analgesic [CA 74 123508g, (1971)];

n=2 or 3 anti-inflammatory, antiedemic, analgesic, antipyretic and sedative—when combined with the enzymes, muramidase and amylase [CA 71 42305z (1969)—refers to French Pat. No. M 5,575];

n=3 increases biodegradability of polyolefins [CA 83 194578b, (1975)—refers to U.S. Pat. No. 3,903,029]; stabilizer for methyl methacrylate polymers [CA 77 140970f (1972)—refers to Japan Pat. No. 72 07 629], n=7 local anesthetic [CA 50 9424 refers to Bull. Soc. Chim. France (1955) 1603–9];

n=8,11 polyester stablizer [CA 76 154779s (1972) refers to Ger. Offen. No. 2,036,712];

n=3,8,11 polyacetal stabilizer [CA 66 29609d (1967)—refers to U.S. Pat. No. 3,288,885];

n=9 desensitizes thermoregulatory reflexes in guinea pigs [CA 72 76596f (1970)—refers to J. Physiol. (London) 206 (3) 495 ∝ 507(1970)];

n=11 thermal stabilizer in resins [CA 86 107522z (1977)—refers to U.S. Pat. No. 4,002,701];

n=15,2-15 antioxidant [CA 58 14257e (1963)—refers to Fr. Pat. No. 1,309,355; CA 48 1714i (1954)—refers to U.S. Pat. No. 2,654,722].

DISCLOSURE OF INVENTION

We have discovered in the course of investigations with experimentally induced inflammation that topical treatment with certain acylaminophenols results in unexpectedly improved suppression of inflammation. They also have local anesthetic properties, particularly when applied to mucous membrane as well as low toxicity in standard tests. The treatment of the present invention can also be used in the therapeutic treatment of a wide variety of dermatological and mucosal disorders in which inflammation is a component. Examples of these diseases are psoriasis, eczema, contact dermatitis, atopic dermatitis, etc. Inflammation accompanying thermal or chemical burns, as well as sunburn are other areas for application of the therapy of this invention, as are diaper rash, insect bite inflammation throat and eye inflammation, pruritus poison ivy inflammation, hemorrhoids and inflammations caused by stoma adhesives, orthopedic casts, etc. Also vesicular diseases, especially those characterized by acantholysis, and other blistering conditions, appear to be particularly susceptible to this therapy.

In accordance with the present invention, there is provided a topical composition for the treatment of inflammatory conditions of the skin or mucous membrane comprising a pharmaceutically acceptable topical vehicle containing an N-acylaminophenol having normal aliphatic side chains of six to twelve carbon atoms. The structural formulas of the n-aliphatic N-acylaminophenols that are the active ingredients in the composition and treatment of this invention and 4-salicylaminophenol a related compound also disclosed and claimed in parent application Ser. No. 92,296, are set forth in formulas I and II below respectively

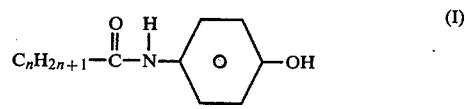

wherein n is an integer from 4 through 11, and

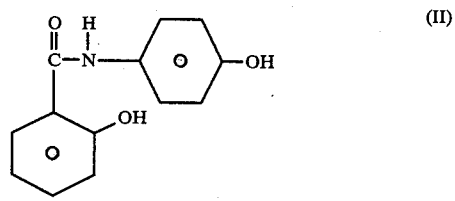

This invention also provides a method of treating inflammatory conditions of the skin comprising topically applying to the affected area a pharmaceutically acceptable topical composition containing an effective amount of an acylaminophenol selected from the compounds of formula I.

DETAILED DESCRIPTION OF THE INVENTION

The concentrations of the active ingredients in the composition will depend upon both the particular compounds used and upon the vehicle. When the vehicle used in propylene glycol/ethanol (30:70 by weight), the concentration of the active ingredients should be from about 0.01% to 10.0%, preferably from about 0.05% to about 5.0%. As indicated, lower or higher concentrations may be appropriate for different drugs and for different vehicles or delivery systems.

In addition to liquid vehicles, which may include sprays as well as nose, ear and eye drops, the topical vehicle may be a cream, lotion, gel or other form acceptable for topical use. Also suitable are throat lozenges, paints, sprays and pastilles. In general, treatment is effected by applying the composition or compositions to the affected area from one to about four times daily until the inflammation is relieved. The duration of treatment will vary with the severity of the condition.

TYPICAL FORMULATIONS (Unless otherwise indicated, throughout this specification, all amounts are by weight.)

A. Topical Creams (oil in water emulsion type)

| Ingredients | Conc. Range (By weight) |
| --- | --- |
| Acylaminophenol | 0.01–10.0 |
| Mineral oil | 3.0–10.0 |
| Cetyl alcohol | 1.0–5.0 |
| Isopropyl myristate | 1.0–5.0 |
| Polyoxyethylene (20) stearate | 1.0–5.0 |
| Propylene glycol | 1.0–60.0 |
| Butylated hydroxyanisole | 0–0.1 |
| Benzoic acid | 0.01–0.5 |

-continued

| Ingredients | Conc. Range (By weight) |
|---|---|
| Sodium edetate | 0.001–0.1 |
| Purified water | q.s. ad–100 |

In these oil-in-water emulsion creams, the cetyl alcohol may be replaced in whole or in part by other fats and waxes such as stearyl alcohol, glyceryl monostearate, spermaceti, white petrolatum, etc. Other emollients which may be used in place of or in addition to the mineral oil and isopropyl myristate include isopropyl palmitate, squalene, and hexadecyl alcohol. Surface-active agents other than polyoxyethylene (20) stearate may include other polyoxyethylene derivatives, sorbitan monoesters, polysorbates with suitable HLB values and other pharmaceutically acceptable surfactants known in the art. Other cosolvents which may be used in place of or in combination with the propylene glycol include glycerin, 1,2,6-hexanetriol, and the liquid polyethylene glycols (300;400). Preservatives other than benzoic acid include the parabens (methyl, propyl or combinations thereof) and sorbic acid. Anti-oxidants other than butylated hydroxyanisole include butylated hydroxytoluene, citric acid and propyl gallate, chelants other than sodium edetate include calcium disodium edetate and ethylenediamine tetraacetic acid (EDTA).

The following is a typical method of preparing the foregoing topical creams.

Oil Phase. Disperse mineral oil in isopropyl myristate in a suitable container (glass lined or stainless steel) heated to 80°–90° C., then add the oil-soluble ingredients such as butylated hydroxyanisole and a portion of the surfactant, and any fats or waxes from the general formula. Continue to heat with stirring until a uniform solution/melt is obtained.

Aqueous Phase. In a separate suitable container, heat the water to 80°–90° C. Then dissolve the benzoic acid and add the propylene glycol and remainder of the surfactant while mixing well.

Emulsification Step Add the water phase to the oil phase at 80°–90° C. and agitate for a sufficient time period to insure complete mixing. Cool to the congealing point and add sufficient water to bring to the correct weight.

Incorporation of Active Ingredients

The acylaminophenol can be incorporated as finely divided micronized powder or dissolved in one of the vehicle ingredients.

B. Solutions

Liquid preparations for topical administration can be prepared in which the acylaminophenol is present in solution form, using pharmaceutically acceptable solvents. Other pharmaceutically acceptable adjuvants, including a stabilizing system intended for maintaining the chemical integrity of the acylaminophenols, may also be included if warranted. The following general formulation is illustrative:

| Ingredients | Conc. Range (By weight) |
|---|---|
| Acylaminophenol | 0.01–10.0 |
| Adjuvant(s) | 0.0–0.2 |
| Solvent(s) | q.s. ad–100 |

The solvent system may contain one or a multiplicity of solvents suitable for topical administration, which may be selected from the lower alcohols (ethanol, isopropanol), glycols such as propylene, ethylene and polyethylene glycols (liquids at room temperature), other organic solvents such as dimethylsulfoxide, dimethylformamide, dimethylacetamide, 1,2,6-hexanetriol, butanediol and other liquid solvents completely or partially miscible with water.

The method of preparation for these solution forms of anti-inflammatory agents is generally (as is known in the art) to dissolve the solid ingredients in the primary solvent using a suitable container (glass or stainless steel lined) and mixers. The resulting solutions can then be filtered to remove extraneous matter and brought to final weight with the co-solvent and/or primary solvent, using the customary precautions to minimize loss of solvent by evaporation.

C. Gels

The above solutions can be made into semisolid (gel) preparations by the use of gelling agents such as hydroxypropyl cellulose, hydroxyethyl cellulose, carbomer polymers, and combinations of the above, according to the following general formula and procedure.

| Ingredients | Conc. Range (By weight) |
|---|---|
| Acylaminophenol | 0.01–10.0 |
| Alcohol | 10.0–70.0 |
| Co-solvent | 0–80.0 |
| Gelling agent | 0.5–5.0 |
| Purified water | q.s. ad–100 |

The gelling agent (e.g., hydroxypropyl cellulose) is added to the solution of acylaminophenol in its solvent system with agitation, while avoiding clumping or excess air entrapment, using a glass-lined or stainless steel container.

D. Ointments

Ointments (water immiscible or water miscible) of the compositions of the invention are typified by the following general formula.

| Ingredients | Conc. Range (By weight) |
|---|---|
| Acylaminophenol | 0.01–10.0% |
| Surfactant | 0–5.0% |
| Solvent | 1.0–20% |
| White petrolatum | q.s. ad–100 |

Typically, the ointment is prepared by heating the white petrolatum in a suitable container (glass-lined or stainless steel) until fluid and adding the active ingredients in any of the following forms: (a) a suspension, in a finely powdered, micronized state, (b) solubilized in a solvent system comprising such solvents as propylene glycol, polyethylene glycol 300, polyethylene glycol 400 or polyethylene glycol 1540 alone or in combination with 1,2,6-hexanetriol, propylene carbonate or other such solvents; with the acylaminophenol solubilized. Suitable oil soluble surfactants, for example, hydroxylated lanolin, ethoxylated lanolin derivatives or polyoxyethylene esters can be added to the petrolatum to make the ointment water miscible, or the surfactants may be omitted to make the ointment water immiscible.

E. Powders

The following is a typical dusting powder formulation containing an acylaminophenol in accordance with the invention.

| Ingredients | Conc. Range (By weight) |
|---|---|
| Acylaminophenol | 0.01–10.0 |
| Talcum powder | 0–99.99 |
| Cornstarch | 0–99.99 |

The acylaminophenol is mixed with the talcum powder and/or cornstarch by adding the latter, preferably in geometric progressions, until the entire mixture is blended uniformly, using a glass-lined or stainless steel container and suitable mixing equipment. Particle size distributions of the acylaminophenol in the range of 5–25 microns are preferred to facilitate a homogeneous mixture.

F. Aerosol

Many types of aerosol formulations can be used as vehicles for the acylaminophenols in accordance with the present invention. These can vary with the type of propellant and concentrate used in the manufacture, as is known to those skilled in the art. The example given below is for a general formula for a quick breaking alcoholic foam.

| | Conc. Range (By weight) |
|---|---|
| Ingredients | |
| Concentrate | |
| Ethoxylated lanolin alcohol | 0.5–2.5 |
| Cetyl alcohol | 0.5–2.5 |
| Acylaminophenol, micronized | 0.01–10.0 |
| Ethanol, USP | 30.0–90.0 |
| Distilled water | 9.49–55.0 |
| Final Product | |
| Concentrate | 80.0–5.0 |
| Propellants 12/114,40:60 | 5.0–20.0 |

The acylaminophenol is either dissolved or dispersed in the ethanol/water solvent system together with the cetyl alcohol and the lanolin derivative. A preservative (e.g., Hyamine 1622) can be added if warranted. The concentrate is then mixed with the propellant, either by cold filling or by pressure filling according to known methods of manufacture.

G. Impregnated Tape

An adhesive tape impregnated with an acylaminophenol of the invention can be prepared using the technology and directions stated in U.S. Pat. No. 3,632,740 issued on Jan. 4, 1972 to R. C. V. Robinson et al. ("Topical Device for the Therapeutic Management of Dermatological Lesions With Steroids"). The acylaminophenol can be added in solution in an appropriate organic solvent.

As indicated above, the acylaminophenol compounds employed in the composition and treatment of the present invention are known compounds. Suitable methods for their preparation are described, for example, in *Helvetica Chimica Acta* 22:82–112 (1939), more particularly at pages 89–93. Generally, p-aminophenol is reacted with the appropriate acid anhydride or chloride.

H. Throat Lozenge—Candy Base

| Micronized acylaminophenol | .01–0.2 gm. |
|---|---|
| Candy Base Q.S. | –2.0 gm. |

The candy base is composed of sucrose and corn syrup solids, food color and flavor.

Method of Preparation

1. The candy base is prepared by metering 345 pounds (46 gallons) of Liquid Sugar No. 1 and 230 lbs. of 43° Baume Corn Syrup into a steam jacketed kettle known as a premelter.
2. The mass is cooked to 238° F. under atmospheric pressure and then pumped into a storage vessel which feeds a National Equipment Continuous Cooker. As the syrup passes through a coil in the cooking chamber, which is surrounded by high pressure steam, it reaches a temperature of 290°–300° F.
3. Batches are delivered to a stainless steel receiving kettle maintained at 28–29 inches of vacuum by means of multi-stage, steam vacuum ejectors for a period of 7 minutes. The vacuum serves to remove additional moisture without additional heat.
4. At this stage, the candy base is composed of approximately:
   64.77% Sugar Solids
   34.63% Corn Syrup Solids
   0.6% Moisture.
5. 300 pounds of candy base is then transferred (150 pounds to each of two), stainless steel mixing kettles, one designated as Part "A" of the batch and the other Part "B."
6. Approved food color Q.S. is divided in two equal parts for mixing with Parts "A" and "B."

Flavor Compound Q.S. is divided in two equal parts for mixing with Parts "A" and "B."

Micronized acylaminophenol to yield 0.5 to 10% of the lozenge is divided into two equal parts for mixing with Parts "A" and "B."

7. The batch is then placed in an automatic batch roller for feeding a Hansella type forming machine which punches out the lozenges. The lozenges are fed through a cooling and hardening conveyor in a dehumidified room. They are then transferred to machines for individual wrapping.

I. Acylaminophenol-Lozenge, Sucrose Base

| Acylaminophenol | 0.02–0.06 gm. |
|---|---|
| Pluronic F68 | 0.40–0.60 gm. |
| Sucrose | 2 gm. |
| Binder Solution Q.S. | |
| Flavor Q.S. | |
| Lubricant Q.S. | |

Method of Preparation

1. Acylaminophenol is dissolved in molten Pluronic F68. The solution is allowed to cool to the solid state and is subsequently pulverized and sieved through #40 mesh screen.
2. Sucrose is pulverized and sieved through a #40 mesh screen.
3. #1 and #2 are mixed then are wet granulated with an appropriate aqueous binder solution, e.g. gum tragacanth, acacia, or methyl cellulose or other binder well known in the art.

4. Flavor, e.g., peppermint oil, plus menthol or cherry flavor are added and mixed.

5. The wet granules are dried in a hot air oven.

6. An appropriate lubricant, e.g., talc or magnesium stearate or stearic acid is added to the dry granulation and mixed.

7. The granulation is compressed in a tablet machine to produce tablets for slow dissolution in the mouth.

As an alternative to the above described (wet granulation) procedure, dry granulation by "slugging" or chilsonating may be substituted.

J. Acylaminophenol Pastille

| Acylaminophenol | 0.01–0.2 gm. |
| Pastille Base | Q.S.–2.0 gm. |

The base may be composed of glycogelatin or other suitable preparations containing gelatin and glycerin, or a mixture of acacia and sucrose. Glycerin in the base may be substituted with propylene glycol.

K. Acylaminophenol Throat Paint

Acylaminophenol (0.5–10%) is dissolved in propylene glycol or glycerin. The final concentration in glycerin or propylene glycol will constitute a saturated solution of acylaminophenol and will vary according to the solubility of the particular acylaminophenol selected, but will provide 0.5–10% concentration in the final solution.

L. Acylaminophenol Throat Spray

| Acylaminophenol | 0.5–10% |
| Flavor | Q.S. |
| Saccharin Sodium | Q.S. |
| Alcohol 50% | Q.S.–100 |
| Propellent | Q.S. |

Propellant may be selected from available propellants known in the art, e.g., chlorofluorocarbons (propellant 114 or propellant 12 or mixtures thereof), $CO_2$, nitrogen with appropriate head space.

Alcohol, 50%, may be substituted with propylene glycol, glycerin or mixtures of alcohol, glycerin and propylene glycol to provide a 0.50–10% solution of the particular acylaminophenol selected.

EXAMPLE 1

The effect of selected compositions on cutaneous inflammation caused by topical application of arachidonic acid was evaluated. In addition to inflammation, the proliferative response of the epidermis treated with arachidonic acid and the compositions was evaluated.

Fourteen acylaminophenols were studied. The drugs were dissolved in propylene glycol plus ethanol (30:70) and were used at 1% concentrations unless otherwise stated. Fourteen groups of five guinea pigs each served as the experimental subjects. The dorsal skin of both ears was treated once daily for four days (9:00 am) with 25 μl 1% solution of AA in propylene glycol/ethanol (30/70). Immediately after this application, one ear of each guinea pig was randomly chosen for application of 25 μl of the test compound, while the contralateral ear received the vehicle, alone. During the four-day experimental period, DNA synthesized was labeled by continuous administration of a radioactive precursor, $^3$H-thymidine (3 i.p. injections/day of 10 μCi each). Erythema developing in response to topical AA was measured daily on a subjective scale of 0 to 3; where 0=none, 1=mild, 2=moderate, and 3=intense. The average erythema scores were plotted as a function of time, and areas under the response curves were determined for expression of total erythema. On the fifth day, animals were killed and six mm diameter circular samples of dorsal skin from the central portion of the treatment sites were harvested and solubilized in NCS® solubilizer. These tissue solutions were acidified and a simple fluor (diphenyloxazole in toluene) was added for determination of radioactivity by liquid scintillation counting. Radioactivity expressed as counts-per-minute (cpm) correlate with the amount of proliferative activity in the epidermis.

RESULTS

It was found that topical application of acetamidophenol (acetaminophen) had no significant effect on AA-induced erythema or proliferation. The application of 4-propionylaminophenol, 4-n-tetradecanoylaminophenol or 4-n-hexadecanoylaminophenol was also without substantial effect. Benzoylaminophenol, an example of a 4-acylaminophenol of an aromatic acid was also inactive in this model.

It was found that 4-n-butyroylaminophenol significantly inhibited AA-induced epidermal proliferation, but was without effect on erythema.

The acylaminophenols with normal aliphatic side chains ranging from six to twelve carbon atoms showed good activity against both AA-induced erythema and proliferation. These included 4-n-hexanoylaminophenol, 4-n-decanoylaminophenol, 4-n-undecanoylaminophenol, and 4-n-dodecanoylaminophenol, 4-n-heptanoylaminophenol, 4-n-octanoylaminophenol, and 4-n-nonanoylaminophenol.

In addition, the 4-acylaminophenol of salicylic acid (4-salicylaminophenol) showed activity against both erythema and proliferation. These data are summarized in Table 1.

TABLE 1

Activity of topical acylaminophenols against arachidonic acid-induced epidermal proliferation and erythema in guinea pig skin.

| Material Tested | cpm S.E. | % Reduction | Total Erythema | % Reduction |
|---|---|---|---|---|
| 1% Acetaminophen | 3140 ± 346 | 8.0 | 5.2 | 0 |
| Vehicle control | 3415 ± 247 | | 5.2 | |
| 1% 4-propionyl-aminophenol | 1777 ± 251 | 2.6 | 5.5 | −14.6 |
| Vehicle control | 1825 ± 160 | | 4.5 | |
| 1% 4-n-butyroyl-aminophenol | 2680 ± 360 | 27.8* | 4.6 | 4.2 |
| Vehicle control | 3716 ± 343 | | 4.8 | |
| 1% 4-n-hexanoyl-aminophenol | 1488 ± 104 | 28.3* | 1.9 | 50.0 |
| Vehicle control | 2076 ± 158 | | 3.8 | |
| 1% 4-n-heptanoyl-aminophenol | 1435 ± 77 | 27.3* | 1.8 | 47.0 |
| Vehicle control | 1973 ± 211 | | 3.4 | |
| 1% 4-n-octanoyl-aminophenol | 1589 ± 361 | 39.1* | 2.7 | 49.0 |
| Vehicle control | 2611 ± 164 | | 5.3 | |
| 1% 4-n-nonanoyl- | 1472 ± 135 | 20.9* | 2.1 | 34.4 |

-continued

| Material Tested | cpm S.E. | % Reduction | Total Erythema | % Reduction |
|---|---|---|---|---|
| aminophenol | | | | |
| Vehicle control | 1860 ± 214 | | 3.2 | |
| 1% 4-n-decanoyl-aminophenol | 1311 ± 48 | 37.5+ | 2.0 | 47.4 |
| Vehicle control | 2098 ± 409 | | 3.8 | |
| 1% 4-n-undecanoyl-aminophenol | 1380 ± 205 | 37.3* | 2.1 | 38.2 |
| Vehicle control | 2202 ± 262 | | 3.4 | |
| 1% 4-n-dodecanoyl-aminophenol | 2487 ± 368 | 29.0* | 3.8 | 29.0 |
| Vehicle control | 3504 ± 328 | | 5.6 | |
| 1% 4-n-tetradecanoyl-aminophenol | 1681 ± 296 | 15.1 | 3.8 | 0.0 |
| Vehicle control | 1980 ± 237 | | 3.8 | |
| 0.56% 4-n-hexadecanoyl-aminophenol | 3275 ± 463 | 15.1 | 4.8 | 14.3 |
| Vehicle control | 3857 ± 329 | | 5.6 | |
| 1% 4-benzoyl-aminophenol | 2214 ± 316 | 4.2 | 3.8 | 20.8 |
| Vehicle control | 2312 ± 409 | | 4.8 | |
| 1% 4-salicyl-aminophenol | 1532 ± 91 | 23.3* | 3.2 | 41.8 |
| Vehicle control | 1998 ± 172 | | 5.5 | |

*Statistically significant reduction in proliferation
+Not significant due to variability As will be apparent to those skilled in the art, and as indicated above, many modifications and variations of the foregoing detailed description are possible within the spirit and scope of the present invention.

Having thus described our invention, what we desire to secure by Letters Patent is defined in the appended claims.

What is claimed is:

1. A method of topical treatment of an inflammatory condition comprising applying to the affected area an anti-inflammatory agent selected from the group consisting of the N-acylaminophenols containing normal aliphatic side chains having from six to twelve carbon atoms in a pharmaceutically acceptable topical vehicle, in an amount sufficient to combat said inflammatory condition.

2. The method of claim 1 wherein said acylaminophenol is selected from the group consisting of 4-n-hexanoylaminophenol, 4-n-heptanoylaminophenol, 4-n-octanoylaminophenol, 4-n-nonanoylaminophenol, 4-n-decanoylaminophenol, 4-n-undecanoylaminophenol and 4-n-dodecanoylaminophenol.

3. The method of claim 2 wherein said topical vehicle comprises a mixture of propylene glycol and ethanol.

4. The method of claim 2 wherein said topical vehicle comprises a mixture of propylene glycol and dimethylsulfoxide.

5. The method of claim 3 wherein said acylaminophenol is present in said vehicle in an amount of from about 0.01% to about 10.0% by weight.

6. The method of claim 4 wherein said acylaminophenol is present in said vehicle in an amount of from about 0.01% to about 10.0% by weight.

7. A composition for the topical treatment of an inflammatory condition comprising a pharmaceutically acceptable topical vehicle selected from the group consisting of nose, ear and eyedrops, creams, lotions, gels, throat lozenges, paint sprays and pastilles containing an anti-inflammatory agent selected from the group consisting of the N-acylaminophenols containing normal aliphatic side chains having from six to twelve carbon atoms, in an amount sufficient to combat said inflammatory condition.

8. The composition of claim 7 wherein said acylaminophenol is selected from the group consisting of 4-n-hexanoylaminophenol, 4-n-heptanoylaminophenol, 4-n-octanoylaminophenol, 4-n-nonanoylaminophenol, 4-n-decanoylaminophenol, 4-n-undecanoylaminophenol and 4-n-dodecanoylaminophenol.

9. The composition of claim 7 wherein said acylaminophenol is present in said vehicle in an amount of from 0.01% to about 10.0% by weight.

10. The composition of claim 7 wherein said vehicle comprises propylene glycol.

11. The composition of claim 7 wherein said vehicle comprises propylene glycol and a member selected from the group consisting of ethanol and dimethylsulfoxide.

* * * * *